United States Patent
Jones et al.

(10) Patent No.: US 12,303,720 B2
(45) Date of Patent: May 20, 2025

(54) GANTRY HAVING A RETRACTABLE COVER

(71) Applicant: Mevion Medical Systems, Inc., Littleton, MA (US)

(72) Inventors: Mark R. Jones, Reading, MA (US); James Cooley, Boxborough, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 190 days.

(21) Appl. No.: 17/865,508

(22) Filed: Jul. 15, 2022

(65) Prior Publication Data

US 2023/0022716 A1    Jan. 26, 2023

Related U.S. Application Data

(60) Provisional application No. 63/223,760, filed on Jul. 20, 2021.

(51) Int. Cl.
*A61N 5/10* (2006.01)

(52) U.S. Cl.
CPC ........... *A61N 5/1081* (2013.01); *A61N 5/107* (2013.01); *A61N 2005/1061* (2013.01)

(58) Field of Classification Search
None
See application file for complete search history.

(56) References Cited

U.S. PATENT DOCUMENTS

| | | | | |
|---|---|---|---|---|
| 4,907,152 A | * | 3/1990 | Lempriere | G01N 23/046 382/293 |
| 6,853,703 B2 | * | 2/2005 | Svatos | A61N 5/1042 378/65 |

(Continued)

FOREIGN PATENT DOCUMENTS

| | | |
|---|---|---|
| CN | 102132280 A | 7/2011 |
| CN | 104307113 A | 1/2015 |

(Continued)

OTHER PUBLICATIONS

Written Opinion of the International Preliminary Examining Authority for International (PCT) Patent Application No. PCT/US2022/073770, issued Feb. 8, 2023, (6 pages).
Buchsbaum, J.C., McDonald, M.W., Johnstone, P.A. et al. Range modulation in proton therapy planning: a simple method for mitigating effects of increased relative biological effectiveness at the end-of-range of clinical proton beams. Radiat Oncol 9, 2 (2014). https://doi.org/10.1186/1748-717X-9-2; (28 pages).

(Continued)

*Primary Examiner* — Marcus H Taningco
*Assistant Examiner* — Djura Malevic
(74) *Attorney, Agent, or Firm* — ArentFox Schiff LLP (57) ABSTRACT

An example particle therapy system includes a toroid-shaped gantry having a central axis. The toroid-shaped gantry has a cover. The cover includes one or more segments that are rotatable at least partly around the central axis of the toroid-shaped gantry to create an unobstructed opening in the toroid-shaped gantry. The particle therapy system includes a patient couch configured to move relative to a hole in the toroid-shaped gantry, an imaging system coupled to an interior of the toroid-shaped gantry and configured for rotation about the hole in the toroid-shaped gantry, where the imaging system is configured to capture images of a patient on the patient couch, and a nozzle coupled to the interior of the toroid-shaped gantry and configured for rotation about the hole in the toroid-shaped gantry. The nozzle is configured to deliver radiation to a target in the patient based on one or more of the images.

27 Claims, 5 Drawing Sheets

(56) References Cited

U.S. PATENT DOCUMENTS

| | | | | |
|---|---|---|---|---|
| 7,154,991 | B2* | 12/2006 | Earnst | A61B 6/548 378/65 |
| 7,166,852 | B2* | 1/2007 | Saracen | A61N 5/1049 250/491.1 |
| 7,298,385 | B2* | 11/2007 | Kazi | B25J 9/1671 700/254 |
| 7,695,192 | B2* | 4/2010 | Henderson | A61B 6/4458 378/198 |
| 7,767,988 | B2* | 8/2010 | Kaiser | A61N 5/1049 378/65 |
| 7,784,127 | B2* | 8/2010 | Kuro | A61B 6/465 5/616 |
| 7,860,550 | B2* | 12/2010 | Saracen | A61B 6/548 5/601 |
| 7,875,861 | B2* | 1/2011 | Huttenberger | A61N 5/1049 5/601 |
| 7,957,508 | B2* | 6/2011 | Brooks | A61B 6/4258 378/65 |
| 8,002,465 | B2* | 8/2011 | Ahn | A61N 5/1049 378/65 |
| 8,160,205 | B2* | 4/2012 | Saracen | A61B 6/0487 378/68 |
| 8,575,563 | B2* | 11/2013 | Cameron | A61N 5/1077 250/397 |
| 8,653,473 | B2* | 2/2014 | Yajima | A61N 5/1081 250/492.1 |
| 8,748,852 | B2 | 6/2014 | Jongen | |
| 8,791,656 | B1* | 7/2014 | Zwart | H05H 13/02 315/501 |
| 8,975,836 | B2* | 3/2015 | Bromberg | H01F 6/06 315/502 |
| 9,326,907 | B2* | 5/2016 | Marle | A61B 6/0407 |
| 9,711,254 | B2* | 7/2017 | Bromberg | G21K 1/093 |
| 9,723,705 | B2 | 8/2017 | Gall et al. | |
| 9,730,308 | B2 | 8/2017 | Zwart et al. | |
| 9,795,361 | B2* | 10/2017 | Marx | B25J 9/1679 |
| 9,833,897 | B2* | 12/2017 | Søe-Knudsen | B25J 9/1682 |
| 9,844,871 | B2* | 12/2017 | Goodwin | B25J 9/06 |
| 9,950,194 | B2* | 4/2018 | Bouchet | A61N 5/1049 |
| 9,986,960 | B2* | 6/2018 | Ay | A61B 6/037 |
| 10,188,356 | B2* | 1/2019 | Guertin | A61B 6/4441 |
| 10,265,544 | B2* | 4/2019 | Bharat | A61B 5/0261 |
| 10,293,186 | B2* | 5/2019 | Sun | A61N 5/1049 |
| 10,463,881 | B2* | 11/2019 | Gerbershagen | H05H 7/04 |
| 10,485,995 | B2* | 11/2019 | Anferov | A61N 5/1077 |
| 10,603,518 | B2* | 3/2020 | Hassan | H05H 7/001 |
| 10,675,487 | B2* | 6/2020 | Zwart | G21K 1/10 |
| 10,688,659 | B2* | 6/2020 | Gomi | B25J 18/00 |
| 10,806,409 | B2* | 10/2020 | Kruesi | A61B 6/0407 |
| 10,806,950 | B2* | 10/2020 | Fahrig | A61N 5/1078 |
| 10,813,816 | B2* | 10/2020 | Yano | A61B 5/055 |
| 11,247,073 | B2* | 2/2022 | Nagamoto | A61B 6/0487 |
| 11,389,669 | B2* | 7/2022 | Traneus | A61N 5/1081 |
| 11,511,135 | B2* | 11/2022 | Debatty | A61B 6/4464 |
| 11,738,210 | B2* | 8/2023 | Wang | A61B 6/032 600/1 |
| 2003/0048875 | A1* | 3/2003 | Mihara | A61N 5/10 378/196 |
| 2004/0172756 | A1* | 9/2004 | Somasundaram | A61B 6/0487 5/601 |
| 2005/0085710 | A1* | 4/2005 | Earnst | A61B 6/0487 378/65 |
| 2005/0226377 | A1* | 10/2005 | Wong | G05B 19/4061 378/65 |
| 2005/0228255 | A1* | 10/2005 | Saracen | A61B 6/548 600/407 |
| 2005/0234327 | A1* | 10/2005 | Saracen | A61B 6/548 600/407 |
| 2006/0106301 | A1* | 5/2006 | Kats | A61N 5/1078 600/415 |
| 2007/0051904 | A1* | 3/2007 | Kaiser | A61N 5/10 250/492.1 |
| 2008/0093567 | A1* | 4/2008 | Gall | H05H 13/02 250/493.1 |
| 2008/0219407 | A1* | 9/2008 | Kaiser | A61N 5/1081 378/65 |
| 2009/0065717 | A1* | 3/2009 | Kaiser | A61N 5/1049 250/505.1 |
| 2011/0085640 | A1* | 4/2011 | Fadler | A61B 6/4441 378/65 |
| 2011/0124976 | A1* | 5/2011 | Sabczynski | G16H 30/20 703/11 |
| 2011/0301449 | A1* | 12/2011 | Maurer, Jr. | A61B 6/032 378/65 |
| 2012/0307973 | A1* | 12/2012 | Dirauf | A61N 5/1049 378/62 |
| 2013/0187060 | A1* | 7/2013 | Jongen | H01J 3/26 250/396 R |
| 2013/0256551 | A1* | 10/2013 | Yao | A61N 5/1082 250/393 |
| 2014/0094638 | A1* | 4/2014 | Gall | A61N 5/1077 315/502 |
| 2014/0371511 | A1* | 12/2014 | Zwart | A61N 5/1077 315/502 |
| 2016/0067525 | A1* | 3/2016 | Bouchet | A61N 5/1069 600/1 |
| 2016/0247591 | A1* | 8/2016 | Bromberg | A61N 5/1077 |
| 2017/0128746 | A1* | 5/2017 | Zwart | A61N 5/1077 |
| 2017/0157426 | A1* | 6/2017 | Buchsbaum | A61N 5/1067 |
| 2018/0064958 | A1* | 3/2018 | Kobayashi | A61N 5/1081 |
| 2019/0308034 | A1* | 10/2019 | Nagamoto | A61B 6/50 |
| 2020/0002980 | A1* | 1/2020 | Ketels | E05B 83/30 |
| 2020/0298025 | A1* | 9/2020 | Cooley, III | A61N 5/1031 |
| 2021/0077828 | A1* | 3/2021 | Wang | A61N 5/1049 |
| 2021/0162236 | A1* | 6/2021 | Shvartsman | G01R 33/3806 |
| 2021/0183728 | A1* | 6/2021 | Bottura | A61N 5/1077 |
| 2022/0249872 | A1* | 8/2022 | Seco | A61N 5/1081 |
| 2022/0347494 | A1* | 11/2022 | Debatty | A61N 5/1049 |

FOREIGN PATENT DOCUMENTS

| | | |
|---|---|---|
| CN | 108290052 A | 7/2018 |
| CN | 111936204 A | 11/2020 |
| EP | 3573075 A1 | 11/2019 |
| JP | H07227435 A | 8/1995 |
| TW | 201934158 A | 9/2019 |
| WO | 2021109920 A1 | 6/2021 |

OTHER PUBLICATIONS

Lucca Bottura, "GaToroid: a Novel Superconducting Compact and Lightweight Gantry for Hadron Therapy". The European Organization for Nuclear Research (CERN) KT Seminar, Co-funded by the CERN Budget for Knowledge Transfer (KT) to Medical Applications, Geneva, Switzerland Nov. 22, 2018, https://dirac.iaea.org; (71 pages).

Written Opinion for International Application No. PCT/US2022/073772, mailed Oct. 28, 2022, (6 pages).

International Search Report for International Application No. PCT/US2022/073772, mailed Oct. 28, 2022, (4 pages).

Office Action for Taiwanese Patent Application No. 111127203, issued Feb. 9, 2023, (with English translation), (5 pages).

International Preliminary Report on Patentability in Application No. PCT/US2022/073770 dated May 4, 2023 (14 pages).

Office Action in Taiwanese Application No. 111127195 dated Jun. 26, 2023 [with English translation], 30 pages.

International Preliminary Report on Patentability in Application No. PCT/US2022/073772 dated Jan. 18, 2024, 8 pages.

Bottura et al., "GaToroid: A novel toroidal gantry for hadron therapy," Nuclear Instruments and Methods in Physics Research, Sec. A, Elsevier BV, vol. 983:164588, DOI: 10.1016/j.nima.2020.164588 (2020), 11 pages.

Buchsbaum et al., "Range modulation in proton therapy planning: a simple method for mitigating effects of increased relative biological effectiveness at the end-or-range of clinical proton beams," Radiat Oncol 9, 2 (2014), DOI: 10.1186/1748-717X-9-2, 10 pages.

(56) References Cited

OTHER PUBLICATIONS

Freeman, T., "GaToroid: a non-rotating gantry for hadron therapy," Physics World, [online] Retrieved from <URL: https://physicsworld.com/a/gatoroid-a-non-rotating-gantry-for-hadron-therapy/> [retrieved on Feb. 8, 2024], (2019), 5 pages.

Felcini et al., "Design of the First HTS Single-Coil Demonstrator of GaToroid Toroidal Gantry for Hadron Therapy," in IEEE Transactions on Applied Superconductivity, vol. 31, No. 5, pp. 1-5, Aug. 2021, Art No. 4400205, doi: 10.1109/TASC.2021.3067808.

Felcini et al. "Magnetic Design of a Superconducting Toroidal Gantry for Hadron Therapy." IEEE Transactions on Applied Superconductivity 30 (2020): 1-5.

Written Opinion for International Application No. PCT/US2022/073770, mailed Oct. 28, 2022, (6 pages).

International Search Report for International Application No. PCT/US2022/073770, mailed Oct. 28, 2022, (4 pages).

\* cited by examiner

GANTRY HAVING A RETRACTABLE COVER

CROSS-REFERENCE TO RELATED APPLICATION

Priority is hereby claimed to U.S. Provisional Application No. 63/223,760, which is titled "Gantry Having A Retractable Cover", and which was filed on Jul. 20, 2021. The contents of U.S. Provisional Application No. 63/223,760 are incorporated into this application by reference.

TECHNICAL FIELD

This specification describes examples of particle therapy systems and gantries for use therein, including gantries having retractable covers.

BACKGROUND

Particle therapy systems use a particle accelerator to generate a particle beam for treating afflictions, such as tumors. Particle therapy systems may use a gantry to direct the particle beam toward a patient. In some examples, a gantry includes a device that supports a radiation delivery apparatus during treatment.

SUMMARY

An example particle therapy system includes a toroid-shaped gantry having a central axis. The toroid-shaped gantry has a cover. The cover includes one or more segments that are rotatable at least partly around the central axis of the toroid-shaped gantry to create an unobstructed opening in the toroid-shaped gantry. The particle therapy system includes a patient couch configured to move relative to a hole in the toroid-shaped gantry, an imaging system coupled to an interior of the toroid-shaped gantry and configured for rotation about the hole in the toroid-shaped gantry, where the imaging system is configured to capture images of a patient on the patient couch, and a nozzle coupled to the interior of the toroid-shaped gantry and configured for rotation about the hole in the toroid-shaped gantry. The nozzle is configured to deliver radiation to a target in the patient based on one or more of the images. The example particle therapy system may include one or more of the following features, either alone or in combination.

The nozzle may be connected via a beam conduit to a remote particle accelerator configured to output the radiation. The remote particle accelerator may be in a same room as the toroid-shaped gantry but not mounted to the toroid-shaped gantry. The beam conduit may include magnetics configured and arranged to direct a particle beam from an output of the particle accelerator to the nozzle.

The example particle therapy system may include an arm to which the patient couch is mounted. The arm may include a first segment, a second segment, and third segment. The first segment may be rotatably coupled to the second segment, and the second segment may be rotatably coupled to the third segment. The patient couch may be being one the third segment. The arm may be controlled to move the patient couch into the unobstructed opening when the cover is retracted so that the patient couch is in a vertex field position. The nozzle may be controlled to direct radiation towards a top of a head of the patient on the patient couch in a vertex field position.

In another example, the particle therapy system may include an arm to which the patient couch is mounted. The arm may include at least two segments that are rotatably connected. The arm may be controllable to move the patient couch into the unobstructed opening so that the nozzle can direct radiation to the patient in a vertex field position (for example, to the top of the patient's head). The arm may be controllable to move the patient couch into the unobstructed opening such that the patient couch is within both the hole and the unobstructed opening. The arm may be controllable to move the patient couch into the unobstructed opening such that the patient couch extends from an interior of the hole into the unobstructed opening. The arm may be controllable to move the patient couch into the unobstructed opening such that the patient couch extends at least part-way along a radius of the toroid-shaped gantry. The arm may be controllable to move the patient couch into the unobstructed opening so that the nozzle can direct radiation to a top of a head of the patient.

The imaging system may be configured to capture three-dimensional (3D) images of the patient. The particle therapy system may include a control system to process the images and to control output of the radiation to the patient based on the images. The control system may be configured to control delivery of the radiation based on also on a treatment plan for the patient. The unobstructed opening may include a quadrant of the toroid-shaped gantry.

Another example particle therapy system includes a toroid-shaped gantry having a cover. The cover includes one or more segments that are rotatable at least partly around a central axis of the toroid-shaped gantry or are otherwise movable to create an unobstructed opening in the toroid-shaped gantry. The particle therapy system also includes a nozzle to deliver radiation to a patient, a patient couch that is controllable to move relative to the toroid-shaped gantry, where the patient couch is for supporting the patient, and a control system to control movement of the patient couch into the unobstructed opening so that the patient is in a vertex field position and so that the nozzle can direct radiation to the patient in the vertex field position. The particle therapy system may include one or more of the following features, either alone or in combination.

The patient couch may be mounted to a movable arm. The arm may include a first segment, a second segment, and third segment. The first segment may be rotatably coupled to the second segment, and the second segment may be rotatably coupled to the third segment. The patient couch may be connected to the third segment. The nozzle may be connected via a beam conduit to a remote particle accelerator configured to output the radiation. The beam conduit may include magnetics configured and arranged to direct a particle beam from an output of the particle accelerator to the nozzle. The particle accelerator may be a synchrocyclotron. The synchrocyclotron may include an active return system. The active return system may include conductive coils that conduct current in a reverse direction to main superconducting coils in the synchrocyclotron. The conductive coils may include superconducting coils. The remote particle accelerator may be in a same room as the toroid-shaped gantry but not mounted to the toroid-shaped gantry.

The particle therapy system may include an imaging system mounted to the toroid-shaped gantry. The imaging system may be configured to capture images of the patient. The control system may be configured to control output of the radiation based the images. The images may include 3D images. The imaging system may be configured to capture images of the patient prior to treatment. The imaging system may be configured to capture images of the patient during treatment.

Any two or more of the features described in this specification, including in this summary section, may be combined to form implementations not specifically described in this specification.

Control of the various systems described herein, or portions thereof, may be implemented via a computer program product that includes instructions that are stored on one or more non-transitory machine-readable storage media and that are executable on one or more processing devices (e.g., microprocessor(s), application-specific integrated circuit(s), programmed logic such as field programmable gate array(s), or the like). The systems described herein, or portions thereof, may be implemented as an apparatus, method, or electronic system that may include one or more processing devices and computer memory to store executable instructions to implement control of the stated functions. The devices, systems, and/or components described herein may be configured, for example, through design, construction, arrangement, placement, programming, operation, activation, deactivation, and/or control.

The details of one or more implementations are set forth in the accompanying drawings and the following description. Other features and advantages will be apparent from the description and drawings, and from the claims.

DESCRIPTION OF THE DRAWINGS

Like reference numerals in different figures indicate like elements.

DETAILED DESCRIPTION

Described herein are example particle therapy systems that include a particle accelerator and a toroid-shaped gantry. The toroid-shaped gantry includes a cover that is retractable or that can otherwise be opened to enable a variety of different patient treatment and imaging positions. The example particle therapy system includes a particle accelerator that may be, but is not limited to, a synchrocyclotron. The toroid-shaped gantry may be configured to deliver a charged particle beam, such as protons or ions output from the particle accelerator, to treat tumors or other conditions in a patient.

The toroid-shaped gantry includes a cover, at least part of which is rotatable at least partly around a central axis of the toroid-shaped gantry. Rotation of the cover in one or more directions creates an unobstructed opening in the toroid-shaped gantry. In an example, the cover is comprised of segments. A first segment of the cover may rotate around the toroid-shaped gantry to coincide partially or wholly with a second segment of the cover, thereby exposing the interior of the toroid-shaped gantry and creating the unobstructed opening. The particle therapy system also includes a treatment couch that is configured to move within the unobstructed opening to position a patient to receive vertex field radiation therapy. In this regard, the vertex field includes a radiation field that covers the top of a patient's head and, thus, enables treatment to be delivered to the top of a patient's head. The treatment couch is also configured to move in and around the toroid-shaped gantry to position a patient to receive coplanar field radiation therapy. In this regard, coplanar radiation therapy includes applying a particle beam to the same plane or layer of an irradiation target possibly from different angles.

The toroid-shaped gantry also includes one or more imaging systems that are configured and controllable to capture images of a patient. For example, the toroid-shaped gantry may enable three-dimensional (3D) imaging and use the resulting images for adaptive radiation therapy using fractionated treatments. In this regard, fractionation includes dividing doses of radiation into fractions and applying the fractions of dose to the same treatment area at different times.

Figure 1:
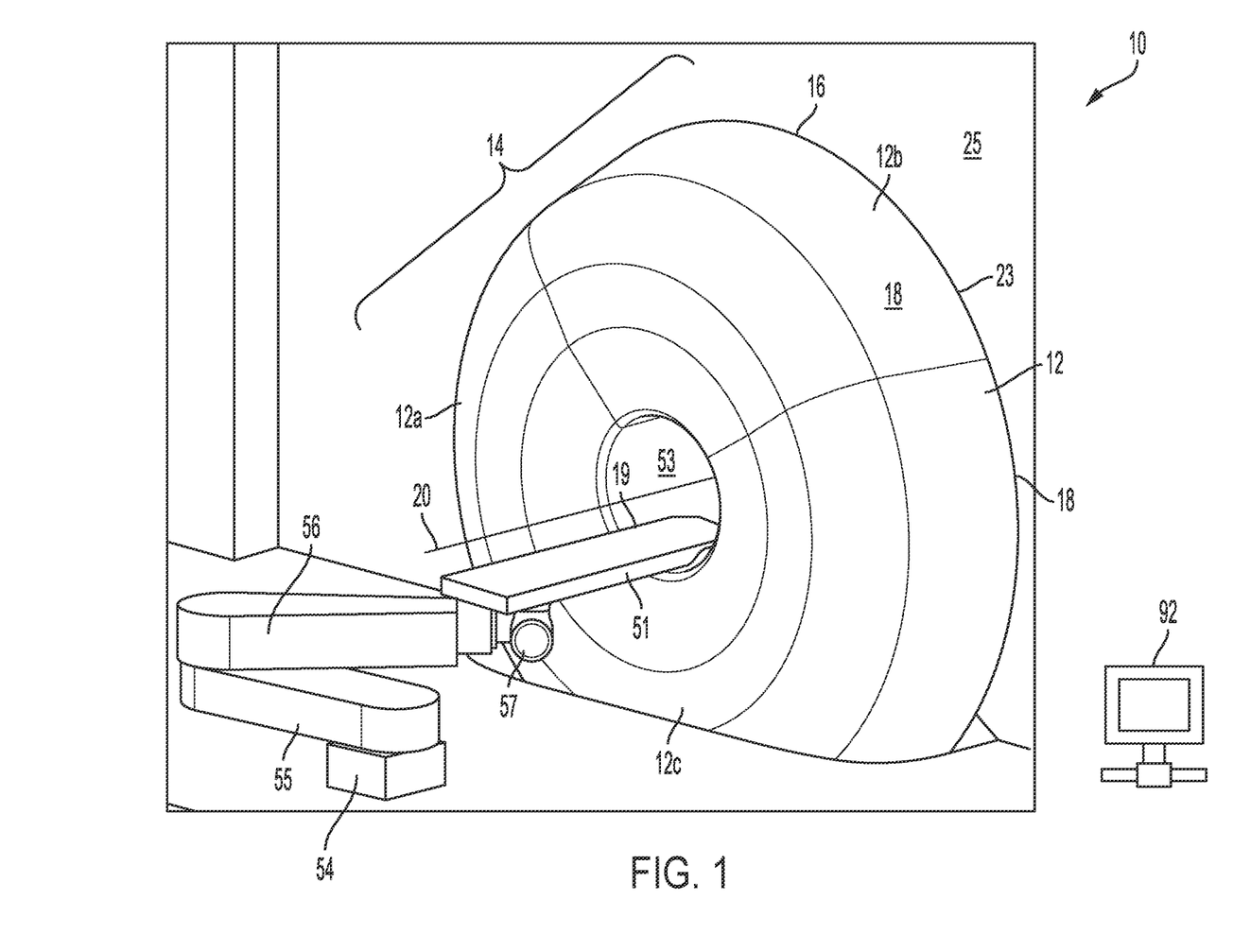
FIG. 1 is a diagram showing a perspective view of an example particle therapy system including an example toroid-shaped gantry of the type described herein.

FIG. 1 shows components of an implementation of a particle therapy system 10 of the type described in the preceding paragraphs. Particle therapy system 10 includes a particle accelerator (not shown), examples of which are described herein. Particle accelerator may be a synchrocyclotron having a superconducting electromagnetic structure that generates a maximum magnet field strength of 3 Tesla (T) or more. A conduit (not shown) delivers particle beam from the particle accelerator to a radiation output device, such as the nozzle described herein, mounted to gantry 14. Example of conduits that may be used are described in U.S. Provisional Application No. 63/151,281 titled "Gantry For A Particle Therapy System", which is incorporated by reference herein. More specifically, examples of conduits that may be used include, but are not limited to, the beamline structures shown in FIGS. 1, 2, 3, 4, 6, 9, 10, and variants thereof, which are described in U.S. Provisional Application No. 63/151,281.

Gantry 14 has a shape that is based on the shape of a toroid. A toroid includes a donut-shape that is formed from surface generated by a closed-plane curve rotated about a line that lies in the same plane as the closed-plane curve. For example, a toroid may be defined parametrically by the following or similar equation set:

$$x(u,v)=(\cos u)(a \cos(v)+c) \qquad (1)$$

$$y(u,v)=(\sin u)(a \cos(v)+c) \qquad (2)$$

$$z(u,v)=a \sin v \qquad (3)$$

for a torus with having center at an origin, a rotational axis of symmetry about a z-axis, a radius c from the center of a hole to a center of a torus tube or opening, and radius a of the tube or opening. In this example, gantry 14 has a generally toroidal shape, as shown in FIG. 1, but need not strictly confirm to the mathematical definition of a toroid.

As shown in FIG. 1, gantry 14 includes an outer shell, referred to herein as cover 16. Cover 16 defines a surface of gantry 14. Cover 16 enables an enclosed architecture, in which gantry 14 encloses a volume within its interior. Cover 16 may also define a hole 53 extending from a front face of gantry 14 through to a backside 23 of gantry 14, which is not visible in the figures, but which extends to and through wall 25.

Cover 16 may be electromagnetically shielded. Shielding effectiveness, that is how well cover 16 reflects, absorbs, or suppresses electromagnetic radiation, is affected by the physical properties of the material that cover 16 includes. In some implementations, cover 16 includes metal such as high permeability steel or stainless steel. In some implementations, cover 16 includes copper, brass, nickel, silver, tin, lead, borated polyethylene, or a combination of two or more of these materials.

Cover 16 may be multi-sectored in that cover 16 may include one or more sections, or segments 18. Segments 18 may be independently movable, for example rotatable around a center axis 20 as described herein. In some implementations, cover 16 may include four segments 18 (which include segments 12, 12a, 12b, 12c), as shown in FIG. 1. In some implementations, cover 16 may include more or fewer segments, for example, two, three, five, six, seven, eight, nine, ten, sixteen, or thirty-two or more segments. Segments 18 may be symmetrically or asymmetrically arranged around cover 16. For example, individual segments may have the same size and shape as shown or different sizes and shapes.

Figure 2:
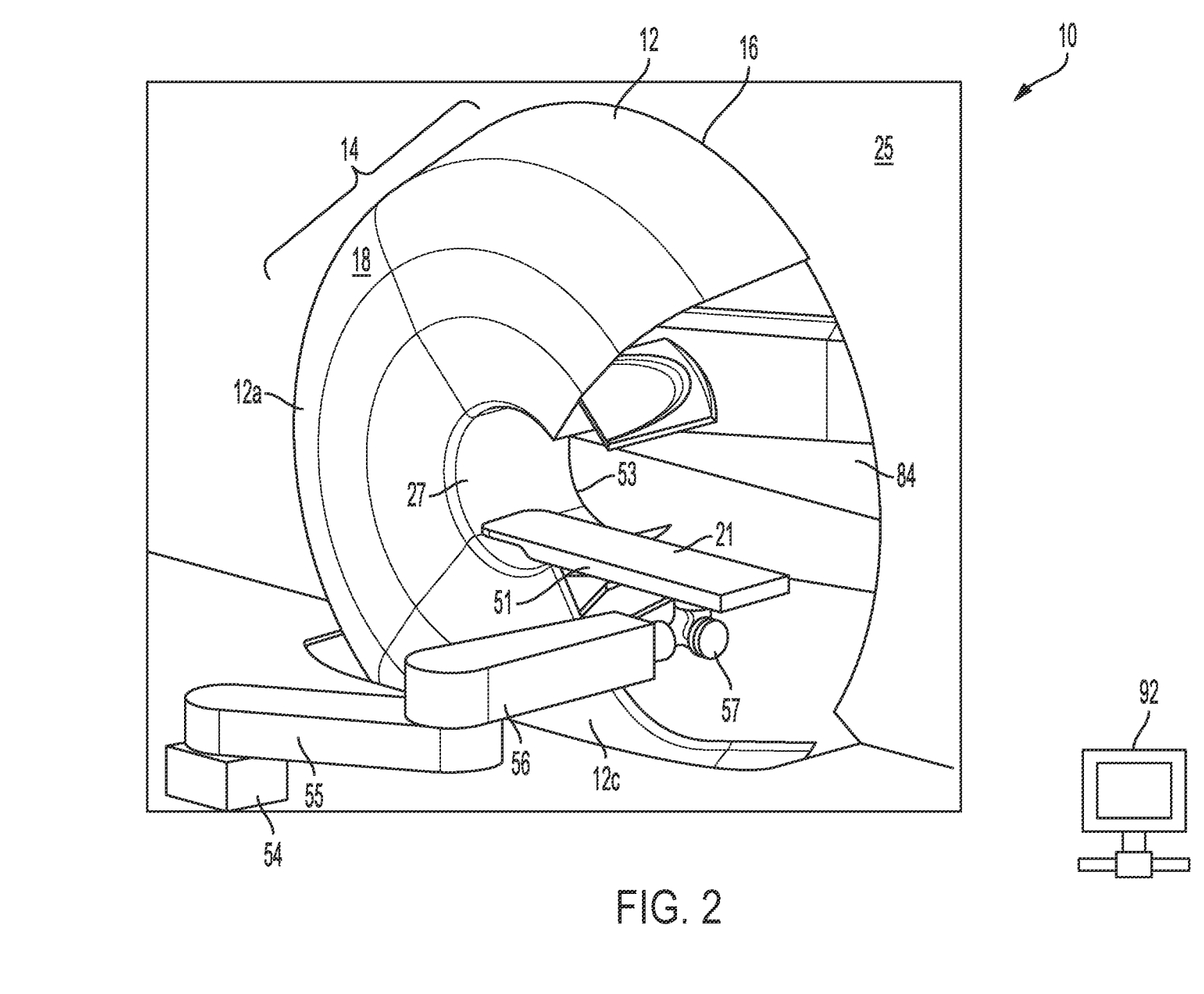
FIG. 2 is a diagram showing a perspective view of the particle therapy system shown in FIG. 1, including the example toroid-shaped gantry with part of its cover retracted to produce an unobstructed opening.
Figure 3:
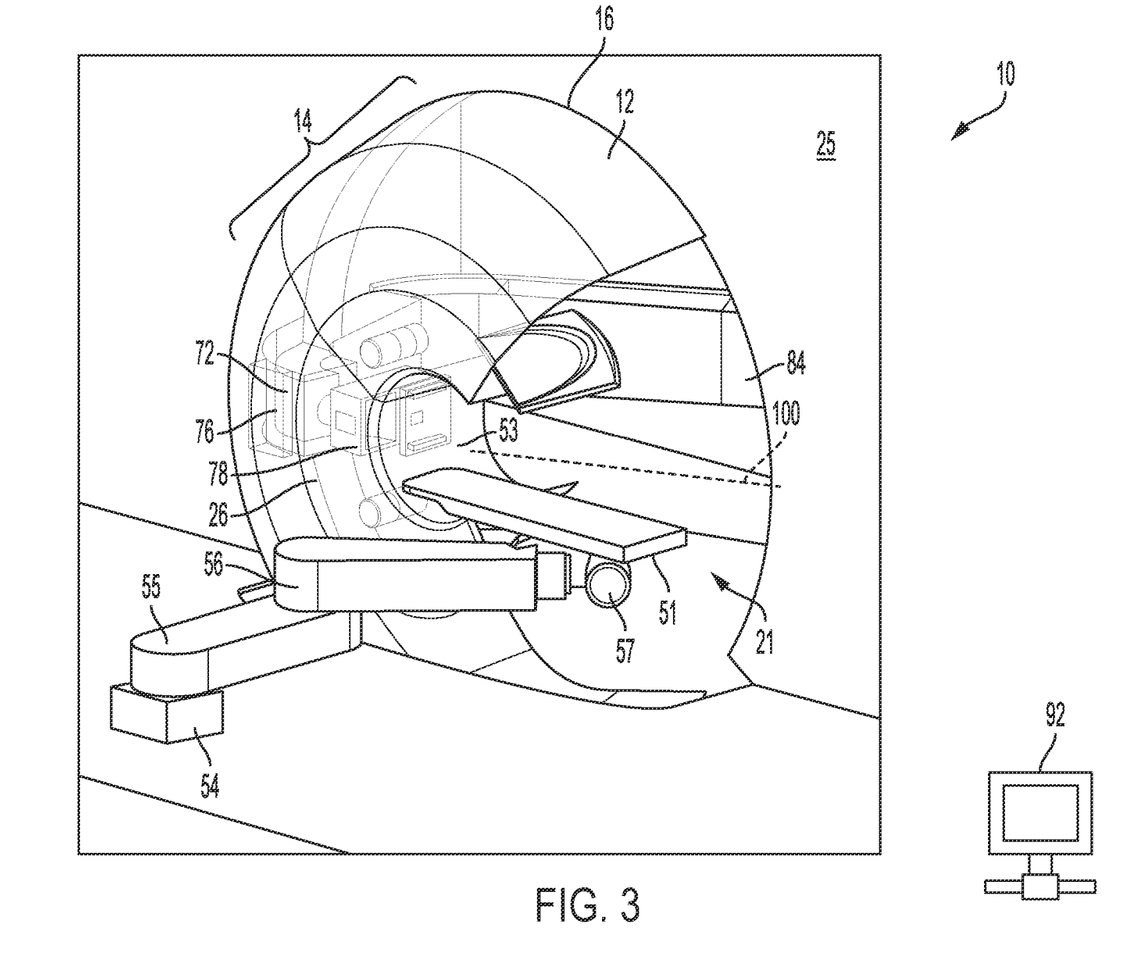
FIG. 3 is a diagram showing a partially transparent perspective view of components in the example toroid-shaped gantry shown in FIGS. 1 and 2.

Referring also to FIGS. 2 and 3, an unobstructed opening, or interior 84 of gantry 14, is accessible by retracting or otherwise moving one of more of segments 18. For example, segment 12 is shown in a closed configuration in FIG. 1. Segment 12 may be configured and controllable to move to an open configuration shown in FIGS. 2 and 3 where, in this example, segment 12 is moved under segment 12b. Segment 12 may thereafter be moved back to a closed configuration.

In this regard, gantry 14 may include rails or tracks (not shown) on its interior 84, or rails or tracks (not shown) on its exterior. For example, the rails or tracks may be on the inside surfaces of one or more, or each of, segments 18. In some implementations, the rails or tracks may be on wall 25 or on another structure that is not part of the gantry. Generally, the rails or tracks are configured and arranged so that, when a segment is moved as shown in FIG. 2 for example, the rails or tracks do not obstruct movement of the patient couch into an area formerly enclosed by that segment.

In an example, segment 12 may configured and controllable to slide along rails or tracks on wall 25 or on an adjacent segment 12b or 12c in either a clockwise direction or a counterclockwise direction around central axis 20. In a particular example, segment 12b may include rails or tracks on its inside surface or its outside surface to which segment 12 is connected and along which segment 12 is controllable to move. During and/or after such movement, segment 12 may move over or under adjacent segment 12b partially or wholly to create the unobstructed opening 84 in the gantry, as shown in FIGS. 2 and 3. In some implementations, gantry 14 may include hinges (not shown) on its interior or hinges (not shown) on its exterior, e.g., on cover 16. The hinges may enable segment 12 to flap open or closed rather than sliding as shown.

One or more—for example, all—of segments 18 may be computer-controlled or controllable by controller 92 to open, to close, to slide, or otherwise to retract or to move to create an unobstructed opening, such as unobstructed opening 84 shown in FIG. 2. As noted, an individual segment may rotate part-way or all the way over or under an adjacent segment. To this end, gantry 14 may include one or more motors to move and to control different segments 18 in the manner described herein. In some implementations, different segments 18 of cover 16 may move at or near the same time so that interior 84 of gantry is exposed by moving two or more segments 18. In this regard, in some implementations multiple adjacent segments may move to create a larger opening or oppositely-arranged segments may move to create two unobstructed openings. For example, two unobstructed openings may be created—one unobstructed opening labeled 84 by moving segment 12 as shown in FIGS. 2 and 3 and one unobstructed openings (not shown) by moving segment 12a (shown closed in the figures) over or under segment 12b or 12c. In some implementations, three segments may move to open 270° of the gantry. For example, segments 12, 12a, and 12b may all move over or under segment 12c. In implementations where there are more than four segments, using such movements more than 270° of the interior of the gantry may be exposed. In implementations where there are fewer than four sectors, using such movements, less than 270° of the interior of the gantry may be exposed.

One or more—for example, all—of segments 18 may be manually-controlled or controllable to open, to close, to slide, or otherwise to retract or to move to create an unobstructed opening, such as unobstructed opening 84 shown in FIG. 2. For example, individual segments may be locked and manually unlocked for movement. In some implementations gantry 14 may include clips, fasteners, or a similar coupling mechanism to attach segments 18 to one another or to another structure. In such implementations, segments 18 may be manually unclipped, unfastened, or otherwise uncoupled and removed from the gantry 14 to produce unobstructed opening 84. Any removed segment or segments 18 may thereafter be clipped, fastened, or otherwise manually coupled back together to enclose opening 84.

In some implementations, one or more robotic arms may be configured and computer-controllable to unclip, to unfasten, or otherwise to uncouple or to move one or more segments 18 from gantry 14 to produce unobstructed opening 84. The one or more robotic arms maybe configured and controllable to reattach the segments.

In some implementations, the interior of the gantry 14 houses both radiation delivery equipment and one or more imaging devices or systems, as shown in FIG. 3. The interior surface 27 of gantry 14 may be made of a transparent material such as plastic or tempered glass that permits transmission of radiation and visible light to enable both delivery or radiation and imaging using various modalities. The interior surface of 27 of gantry 14 may be open, without any covering material.

In some implementations, one or more of the imaging devices or systems 72 may be mounted to a circular track (not shown) or ring on wall 25 and may be controllable to rotate around central axis 20. In some implementations, one or more of the imaging devices or systems 72 may be mounted to a circular track or ring 26 on the interior of gantry 14 and may be controllable to rotate around central axis 20. In some implementations, the circular track, or ring, is stationary and the imaging devices rotate around it, and in some implementations, the circular track, or ring, is rotatable and the imaging devices are stationary on the circular track or ring and rotate with the circular track or ring. In some implementations, the circular track or ring rotates and the imaging devices also rotate around the circular track or ring. In any case, a portion of the track or ring may be retractable along with each segment. For example, if segment 12 is retracted as shown in FIGS. 2 and 3, the portion of the track contained in segment 12 is also retracted in order not to obstruct opening 84 as described herein. The portion of the track may be retracted under an adjacent segment 12b, for example.

Imaging may be performed before and/or during treatment to identify a target location within the patient and to control operation of the gantry 14 and scanning in order to direct a particle beam to the irradiation target in the patient. In this regard, image-guided radiation therapy (IGRT) includes the use of imaging during radiation treatment to improve the precision and accuracy of treatment delivery. IGRT may be used to treat tumors in areas of the body that move, such as the lungs. The toroidal gantry described herein enables IGRT among other imaging techniques.

An example imaging device 72 may include, but is not limited to, one or more computed tomography (CT) systems, one or more fan-beam CT systems, one or more radiograph systems, and the like. Imaging device 72 may be configured and controlled to rotate at least part-way around gantry 14 in response to commands from a control system, such as controller 92. A variety of two-dimensional (2D) and/or three-dimensional (3D) imaging devices 72 also may be mounted on track or ring 26 and rotatable therewith. In some implementations, imaging devices 72 may be mounted to different internal circumferential tracks or rings within the toroid-shaped gantry 14. For example, a first imaging device may be rotatable around a circumferential track at a first radius and a second imaging device may be rotatable around a different circumferential track at a second radius, which is different from the first radius. In some implementations, gantry 14 may include one or more rotatable inner rings, to mount an imaging device 72 or imaging systems for rotation.

In some implementations, imaging device 72 may include two 2D imaging devices, mounted to the interior of gantry 14. For example, two planes of orthogonal 2D imaging may be used for 2D image-guided radiation therapy (IGRT) and can be rotated for cone-beam computed tomography systems (CBCT) acquisition including simultaneously-acquired dual-energy imaging. The imaging devices may also, or alternatively, include an X-ray source and an image panel for CBCT acquisition or a fan-beam diagnostic quality computed tomography (CT) device. Alternatively, one of the two planes may include a CBCT and another of the two planes may include fan-beam diagnostic quality CT.

In some implementations, one or more radiation output devices may be mounted to the interior of gantry 14. A radiation output device such as nozzle 78 (FIG. 3) is located at the exit of a radiation source or delivery conduit (not shown). In the example of FIG. 3, nozzle 78 is configured and controllable to move along gantry 14 to rotate around central axis 20 (FIG. 1) and, thus, the patient. Nozzle 78 receives the particle beam and, in some implementations, conditions the particle beam for output to an irradiation target, such as a tumor in a patient, at treatment position 19 or 21.

In this regard, nozzle 78 may include one or more scanning magnets to move the particle beam across a beam field. In some examples, the beam field is the maximum extent that the particle beam can be moved across a plane parallel to the treatment area on a patient for a given angular position on gantry 14. In some implementations, the scanning magnets may be housed in the beam conduit as described in U.S. Provisional Application No. 63/151,281 incorporated by reference herein.

Nozzle 78 may also include an energy degrader that receives a scanning or moving particle beam from the scanning magnets. The energy degrader may be mounted to gantry 14 (via nozzle 78) between the scanning magnets and the irradiation target at treatment position 19, 21. The energy degrader is configured to, and controllable to, change an energy of the particle beam before the particle beam reaches the irradiation target. For example, the energy degrader may include plates that are movable into or out of a path of the particle beam. For example, the energy degrader may include wedges that overlap at least in part and that are movable within a path of the particle beam. An example wedge is a polyhedron defined by two triangles and three trapezoidal faces. In either configuration, variable amounts of material are movable into the path of the particle beam. The material absorbs energy from the particle beam, resulting reduced-energy beam output. The more material there is in the path of the particle beam, the less energy that the particle beam will have. In some implementations, the energy-absorbing structures are movable across all of the beam field or across only part of the beam field.

Figure 4:
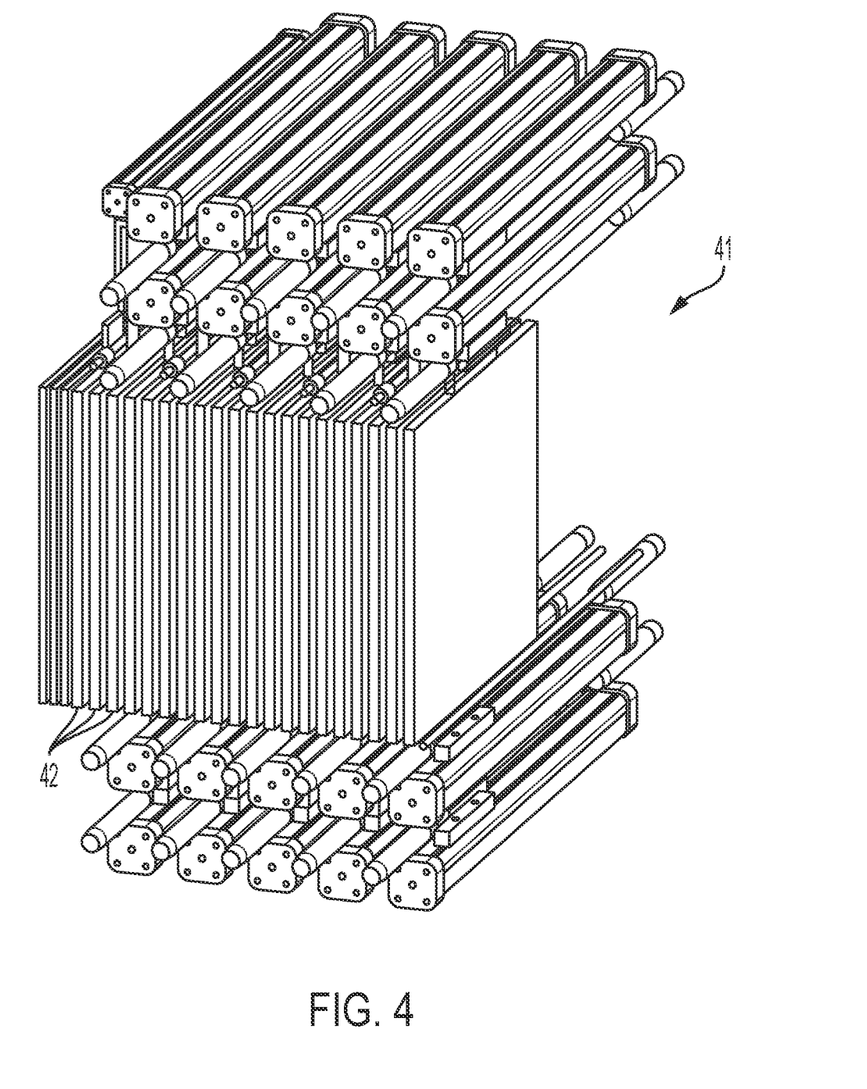
FIG. 4 is a perspective view of an example energy degrader.

Referring to FIG. 4, in an example, energy degrader is a range modulator that is controllable to move structures 42 into, and out of, the path of the particle beam to change the energy of the particle beam and therefore the depth to which dose of the particle beam will be deposited in the irradiation target. Examples of such structures include, but are not limited to, energy-absorbing plates; polyhedra such as wedges, tetrahedra, or toroidal polyhedra; and curved three-dimensional shapes, such as cylinders, spheres, or cones. In this way, the energy degrader can cause the particle beam to deposit doses of radiation in the interior of an irradiation target to treat layers or columns of the target. In this regard, when protons move through tissue, the protons ionize atoms of the tissue and deposit a dose along their path. The energy degrader thus is configured to move the particle beam in the Cartesian Z dimension through the target, thereby enabling scanning in three dimensions. In some implementations, the energy degrader may be configured to move during movement of the particle beam and to track or to trail the particle beam during movement. An example energy degrader that tracks or trails particle beam movement is described in U.S. Pat. No. 10,675,487 (Zwart) entitled "High-Speed Energy Switching". The content of U.S. Pat. No. 10,675,487, particularly the content related to the energy degrader that tracks or trails particle beam movement (e.g., FIGS. 36 to 46 of U.S. Pat. No. 10,675,487 and the accompanying description), is incorporated herein by reference.

The Bragg peak is a pronounced peak on the Bragg curve that plots the energy loss of ionizing radiation during its travel through tissue. The Bragg peak represents the depth at which most protons deposit within tissue. For protons, the Bragg peak occurs right before the particles come to rest. Accordingly, the energy of the particle beam may be changed to change the location of its Bragg peak and, therefore, where a majority of the dose of protons will deposit in depth in the tissue. In this regard, in some implementations, the particle accelerator is a fixed-energy particle accelerator. In a fixed-energy particle accelerator, the particle beam always exits the particle accelerator at the same, or about the same, energy—for example, within a 5% deviation or less from an expected or target energy. In a fixed-energy particle accelerator, the energy degrader is the primary vehicle for varying the energy of the beam applied to an irradiation target in the patient. In some implementations, the particle accelerators described herein are configured to output particle beams at a single energy or at two or more energies within a range between about 100 MeV and about 300 MeV (for example, between 115 MeV and 250 MeV). The fixed energy output may be within that range (e.g., 250 MeV) or, in some examples, above or below that range.

In some implementations, the particle accelerator is a dual-energy accelerator. In a dual-energy particle accelerator, the particle beam exits the particle accelerator at one of two different energy levels—a high energy level and a low energy level. The terms "high" and "low" have no specific numerical connotations but rather are intended to convey relative magnitudes. In some implementations, the particle accelerators described herein are configured to output particle beams at two energies that are within a range that is between about 100 MeV and about 300 MeV. The high energy output and the low energy output may be values within that range or, in some examples, above or below that range. The energy degrader described herein may be used with dual-energy particle accelerators in order to reduce the energy of the particle beam below one of the two energy levels and/or to finely adjust the two energy levels.

Nozzle 78 may also include a collimator downstream of the energy degrader relative to the irradiation target (that is, closer to the target). In an example, a collimator is a structure that is controllable to allow some radiation to pass to a patient and to block some radiation from passing to the patient. Typically, the radiation that passes is directed to an irradiation target to be treated, and the radiation that is blocked would otherwise hit, and potentially damage, healthy tissue. In operation, the collimator is placed in the radiation path between the energy degrader and the irradiation target and is controlled to produce an opening of an appropriate size and shape to allow some radiation to pass through the opening to the irradiation target, while a remainder of the structure blocks some radiation from reaching adjacent tissue. An example of a configurable collimator that may be used is described in U.S. Patent Publication No. 2017/0128746 (Zwart) entitled "Adaptive Aperture". The content of U.S. Patent Publication No. 2017/0128746, particularly the content relating to the description of the adaptive aperture (e.g., FIGS. 1 to 7 of U.S. Patent Publication No. 2017/0128746 and the accompanying description), is incorporated herein by reference.

As with imaging device 72, in some implementations, nozzle 78 may be mounted on or coupled to a circular track or ring 26 and is rotatable therewith within interior 84. In some implementations, imaging device 72 and nozzle 78 may be mounted to the same circular track or ring—for example, to different sides of that circular track or ring. In some implementations, nozzle 78 may be mounted to a different circular track or ring than imaging device 72. As above, the circular track, or ring, may be stationary and the nozzle may rotate around it, and in some implementations, the circular track, or ring, may be rotatable and the nozzle may be stationary on the circular track or ring and rotate with the circular track or ring. In some implementations, the circular track or ring rotates and the nozzle also rotate around the circular track or ring. In any case, a portion of the track or ring may be retractable along with each segment as explained previously. For example, if segment 12 is retracted as shown in FIGS. 2 and 3, the portion of the track or ring contained in segment 12 is also retracted in order not to obstruct opening 84 as described herein. The portion of the ring or track may be retracted under an adjacent segment 12b, for example. The nozzle and imaging devices thus may also move away from opening 84.

In some implementations, nozzle 78 may not rotate around gantry 14. Instead, nozzle 78 may remain stationary, thereby providing a particle beam that is fixed in one direction. This is known as a fixed-beam system. In implementations such as these, a treatment couch 51 or other seat holding the patient moves relative to the fixed beam during treatment. In the system described herein, the location of the particle beam may be set to an angular position on toroid-shaped gantry 14, after which the beam remains fixed except for scanning movements across the irradiation target. The treatment couch 51 or other seat moves during treatment to position the particle beam relative to the target. In some implementations, treatment may be implemented using a combination of toroid-shaped gantry 14 movement and treatment couch 51 (or other seat movement). For example, the imaging device 72 or nozzle 78 may be positioned and the beam may be fixed temporarily, during which time the treatment couch 51 moves to implement treatment. After that, the nozzle may be repositioned to fix the beam temporarily at a new position. Treatment may be implemented at the new position through couch 51 movement. These operations may be repeated as defined by a treatment plan drafted for use with the particle therapy system.

Gantry 14 may include one or more motors (not shown) for moving imaging device 72 and/or nozzle 78 relative to a treatment position. For example, motors may move imaging device 72 and/or nozzle 78 along a track or ring on gantry 14 to rotate imaging device 72 and/or nozzle 78 relative to treatment position 19 or treatment position 21. In some implementations, the rotation enabled by gantry 14 allows imaging device 72 and/or nozzle 78 to be positioned at any angle relative to treatment position 19 or treatment position 21. For example, imaging device 72 and/or nozzle 78 may rotate through 360° and, as such, imaging device 72 and/or nozzle 78 may be positioned at 0°, 90°, 270° or any angle among these rotational positions.

As shown in FIGS. 1 to 3, particle therapy system 10 includes treatment couch 51. Treatment couch 51 is configured to move relative to hole 53 in or through gantry 14. Treatment couch 51 may be mounted on a robotic arm 54 as described below so that treatment couch 51 may move the patient into a treatment position.

In an example treatment position 19, a patient lies on treatment couch 51 and travels along with the patient couch partially or wholly into hole 53 in or through gantry 14. Nozzle 78 is configured to move around gantry 14 as described herein and in accordance with a treatment plan to position nozzle 78 for treatment. Nozzle 78 delivers a particle beam from the particle accelerator to an irradiation target in the patient. In an example, the treatment may include coplanar field radiation therapy. For example, the particle beam may be delivered from nozzle 78 toward the irradiation target to treat a plane or layer in an irradiation target from one or more angles Similarly, before, during, or after treatment, imaging device 72 may capture images of the patient in the treatment position. Imaging may be performed by imaging device 72 before and/or during treatment to identify a target location within the patient and to control operation of the gantry 14 and scanning in order to direct a particle beam to the irradiation target in the patient. As such, imaging device 72 may move or remain stationary or travel along the track or ring within the interior of gantry 14.

Referring to FIGS. 2 and 3, treatment couch 51 is also configured to move relative to, into, and through unobstructed opening 84. In this example, segment 12 or another combination of one or more segments 18 may move from a closed configuration to an open configuration, as explained previously. Treatment couch 51 is controllable to move to, through, and into this unobstructed opening 84. For example, arm 54 is controllable to move the patient couch into the unobstructed opening and the nozzle 78 is controllable to move around gantry 14 to direct radiation to the patient in a vertex field position. For example, arm 54 is controllable to move the patient couch into the unobstructed opening such that the patient couch is within both hole 53 and unobstructed opening 84, as shown in FIGS. 2 and 3. For example, arm 54 is controllable to move the patient couch into the unobstructed opening such that the patient couch extends from an interior of hole 84 into unobstructed opening 84, as shown in FIGS. 2 and 3. For example, arm 54 is controllable to move the patient couch into unobstructed opening 84 such that the patient couch extends at least part-way along a radius 100 of toroid-shaped gantry 14. For example, arm 54 is controllable to move the patient couch into unobstructed opening 84 so that the nozzle can direct radiation to a top of the patient's head (e.g., the vertex position). Nozzle 78 is configured to move continuously, periodically, or to stop at a position within the gantry in accordance with a treatment plan to position the nozzle for treatment of the patient at an appropriate angle. As noted, that angle may be to deliver radiation towards the top of a patient's head. That angle may be to deliver radiation to any target in the patient that would be accessible when the patient is at least partly within the unobstructed opening. For example, the radiation may be delivered to the top of the patient's shoulder or to other parts of the patient's head that are not accessible absent movement into the unobstructed opening.

As noted, treatment couch 51 may be mounted to a robotic arm 54. Arm 54 may be controlled by controller 92. Arm 54 includes a first segment 55, a second segment 56, and third segment 57. First segment 55 is rotatably coupled to second segment 56 and second segment 56 is rotatably coupled to third segment 57. Treatment couch 51 is coupled to third segment 57 as shown in the figure. Arm 54 is controllable to move treatment couch 51 in and through hole 53 to position a patient lying on the couch for treatment; that is, to move the patient into the treatment position. Similarly, arm 54 is controllable to move treatment couch 51 in and through hole 53 and unobstructed opening 84 of toroid-shaped gantry 14 to position a patient lying on the couch for treatment; that is, to move the patient into treatment position 21. In some implementations, arm 54 may position the patient in two degrees of freedom, in three degrees of freedom, in four degrees of freedom, in five degrees of freedom, or in six degrees of freedom. An example of two degrees of freedom is forward-backward movement and left-right movement; an example of three degrees of freedom is forward-backward movement, left-right movement, and up-down movement; an example of four degrees of freedom is forward-backward movement, left-right movement, up-down movement and one of pitch, yaw, or roll movement; an example of five degrees of freedom is forward-backward movement, left-right movement, up-down movement and two of pitch, yaw, or roll movement; and an example of six degrees of freedom is forward-backward movement, left-right movement, up-down movement, pitch movement, yaw movement, and roll movement. In some implementations, the treatment couch may be replaced by a couch that inclines at least in part or by a chair, either of which may be controllable in two, three, four, five, or six degrees of freedom to position the patient for treatment. In some implementations, arm 54 may have a different configuration than that shown in FIG. 1. For example, arm 54 may have two segments or more than three segments. Hydraulics, robotics, or both, may control or implement non-planar movement of the treatment couch.

Particle therapy system 10 may be an intensity-modulated proton therapy (IMPT) system. IMPT systems enable spatial control of circumscribed beams of protons that may have a variable energy and/or intensity. IMPT takes advantage of the charged-particle Bragg peak—as noted, the characteristic peak of dose at the end of particles' delivery range—combined with the modulation of pencil beam variables to create target-local modulations in dose that achieve objectives set forth in a predefined treatment plan. IMPT may involve directing particle beams toward the irradiation target at different angles and at different intensities to treat the target. In some implementations, the particle beam may be scanned—for example, moved—across layers of the irradiation target, with each layer being treated one or more times from the same or different angles. Movement across the irradiation target to implement scanning may be performed using the scanning magnet(s) in a beam conduit.

Figure 5:
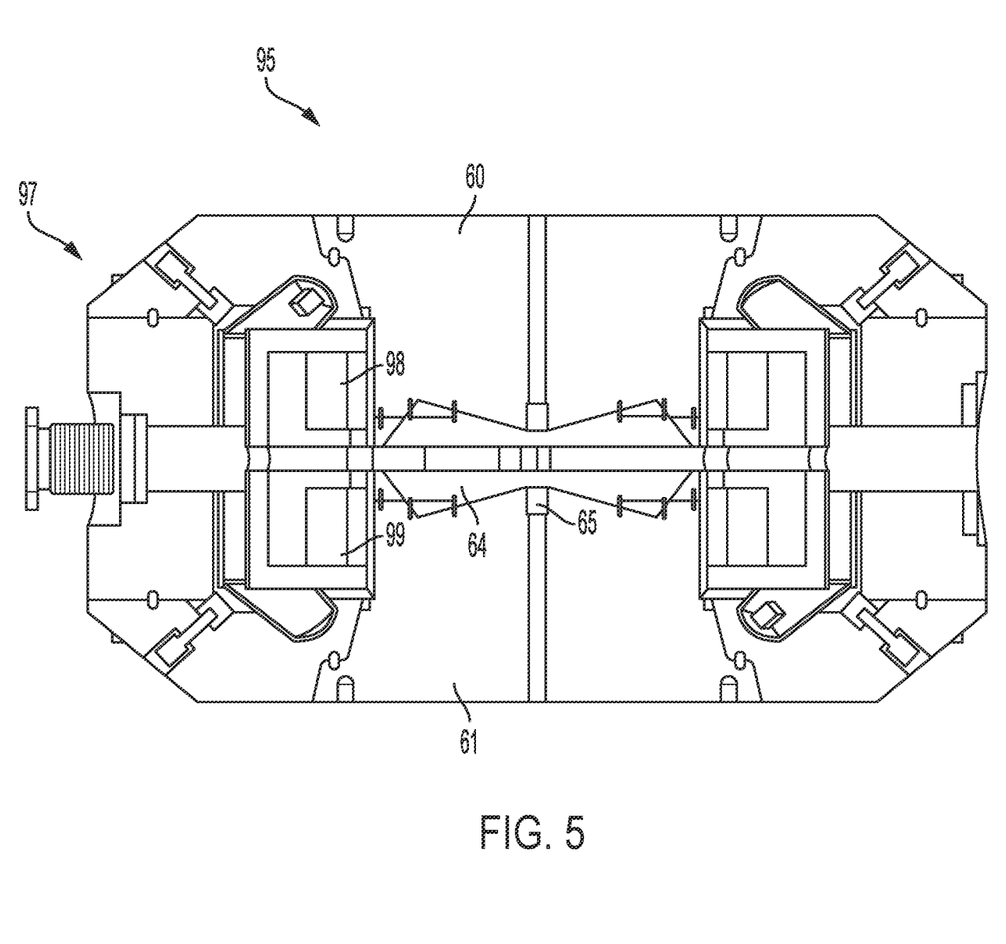
FIG. 5 is a cut-away, side view of components in a particle accelerator that may be used with the particle therapy system.

As described herein, an example proton therapy system scans a proton beam in three dimensions across an irradiation target in order to destroy malignant tissue. FIG. 5 shows a cross-section of components 95 of an example superconducting synchrocyclotron that may be used to provide a particle (e.g., a proton) beam in the proton therapy system. In this example, components 95 include a superconducting magnet 97. The superconducting magnet includes superconducting coils 98 and 99. The superconducting coils are formed of multiple integrated conductors, each of which includes superconducting strands—for example, four strands or six strands—wound around a center strand which may itself be superconducting or non-superconducting. Each of the superconducting coils 98, 99 is for conducting a current that generates a magnetic field (B). The magnetic yokes 60, 61 or smaller magnetic pole pieces shape that magnetic field in a cavity 64 in which particles are accelerated. In an example, a cryostat (not shown) uses liquid helium (He) to conductively cool each coil to superconducting temperatures, e.g., around 4° Kelvin (K).

In some implementations, the particle accelerator includes a particle source 65, such as a Penning Ion Gauge—PIG source, to provide an ionized plasma column to cavity 64. Hydrogen gas, or a combination of hydrogen gas and a noble gas, is ionized to produce the plasma column. A voltage source provides a varying radio frequency (RF) voltage to cavity 64 to accelerate particles from the plasma column within the cavity. As noted, in an example, the particle accelerator is a synchrocyclotron. Accordingly, the RF voltage is swept across a range of frequencies to account for relativistic effects on the particles, such as increasing particle mass, when accelerating particles within the acceleration cavity. The RF voltage drives a dee plate contained within the cavity and has a frequency that is swept downward during the accelerating cycle to account for the increasing relativistic mass of the protons and the decreasing magnetic field. A dummy dee plate acts as a ground reference for the dee plate. The magnetic field produced by running current through the superconducting coils, together with sweeping RF voltage, causes particles from the plasma column to accelerate orbitally within the cavity and to increase in energy as a number of turns increases.

The magnetic field in the cavity is shaped to cause particles to move orbitally within the cavity. The example synchrocyclotron employs a magnetic field that is uniform in rotation angle and falls off in strength with increasing radius. In some implementations, the maximum magnetic field produced by the superconducting (main) coils may be within the range of 3 Tesla (T) to 20 T at a center of the cavity, which falls off with increasing radius. For example, the superconducting coils may be used in generating magnetic fields at, or that exceed, one or more of the following magnitudes: 3.0 T, 3.1 T, 3.2 T, 3.3 T, 3.4 T, 3.5 T, 3.6 T, 3.7 T, 3.8 T, 3.9 T, 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5

T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, the superconducting coils may be used in generating magnetic fields that are outside the range of 3 T to 20 T or that are within the range of 3 T to 20 T but that are not specifically listed herein.

In some implementations, such as the implementations shown in FIG. 5, the relatively large ferromagnetic magnetic yokes 60, 61 act as magnetic returns for stray magnetic fields produced by the superconducting coils. In some systems, a magnetic shield (not shown) surrounds the yokes. The return yokes and the shield together act to reduce stray magnetic fields, thereby reducing the possibility that stray magnetic fields will adversely affect the operation of the particle accelerator.

In some implementations, the return yokes and shield may be replaced by, or augmented by, an active return system. An example active return system includes one or more active return coils that conduct current in a direction opposite to current through the main superconducting coils. In some example implementations, there is an active return coil for each superconducting main coil, e.g., two active return coils—one for each main superconducting coil. Each active return coil may also be a superconducting coil that surrounds the outside of a corresponding main superconducting coil concentrically. By using an active return system, the relatively large ferromagnetic magnetic yokes 60, 61 can be replaced with magnetic pole pieces that are smaller and lighter. Accordingly, the size and weight of the synchrocyclotron can be reduced further without sacrificing performance. An example of an active return system that may be used is described in U.S. Pat. No. 8,791,656 (Zwart) entitled "Active Return System". The content of U.S. Pat. No. 8,791,656, particularly the content related to the return coil configuration (e.g., FIGS. 2, 4, and 5 of U.S. Pat. No. 8,791,656 and the accompanying description), is incorporated herein by reference.

Another example of a particle accelerator that may be used in the particle therapy system herein is described in U.S. Pat. No. 8,975,836 (Bromberg) entitled "Ultra-Light Magnetically Shielded High-Current, Compact Cyclotron". The content of U.S. Pat. No. 8,975,836, particularly the content related to "cyclotron 11" or "iron-free cyclotron 11" of FIGS. 4, 17 and 18 of U.S. Pat. No. 8,975,836 and the accompanying description, is incorporated herein by reference.

In some implementations, the synchrocyclotron used in the proton therapy system described herein may be a variable-energy synchrocyclotron. In some implementations, a variable-energy synchrocyclotron is configured to vary the energy of the output particle beam by varying the magnetic field in which the particle beam is accelerated. For example, the current may be set to any one of multiple values to produce a corresponding magnetic field. For example, the current may be set to one of two values to produce the dual-energy particle accelerator described previously. In an example implementation, one or more sets of superconducting coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In some implementations, some sets of coils, such as the set for the fixed electrical current, are superconducting, while other sets of coils, such as the one or more sets for the variable current, are non-superconducting (e.g., copper) coils.

Generally, in a variable-energy synchrocyclotron, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The step-wise adjustment can produce the dual energies described previously. In some implementations, each step is between 10 MeV and 80 MeV. The scaling of the magnetic field to the current can allow the variation of the beam energy to be carried out relatively precisely, thus reducing the need for an energy degrader. An example of a variable-energy synchrocyclotron that may be used in the particle therapy systems described herein is described in U.S. Pat. No. 9,730,308 entitled "Particle Accelerator That Produces Charged Particles Having Variable Energies". The content U.S. Pat. No. 9,730,308 is incorporated herein by reference, particularly the content that enables operation of a synchrocyclotron at variable energies, including the content described in columns 5 through 7 of U.S. Pat. No. 9,730,308 and FIG. 13 and its accompanying description.

In implementations of the particle therapy system that use a variable-energy synchrocyclotron, controlling the energy of the particle beam to treat a portion of the irradiation target may be performed in accordance with the treatment plan by changing the energy of the particle beam output by the synchrocyclotron. In such implementations, a range modulator may or may not be used. For example, controlling the energy of the particle beam may include setting the current in the synchrocyclotron main coils to one of multiple values, each which corresponds to a different energy at which the particle beam is output from the synchrocyclotron. A range modulator may be used along with a variable-energy synchrocyclotron to provide additional changes in energy, for, example, between discrete energy levels provided by the synchrocyclotron.

The particle therapy system and its variations described herein may be used to apply ultra-high dose rates of radiation—so called, "FLASH" dose rates of radiation—to an irradiation target in a patient. In this regard, experimental results in radiation therapy have shown an improvement in the condition of healthy tissue subjected to radiation when the treatment dose is delivered at ultra-high (FLASH) dose rates. In an example, when delivering doses of radiation at 10 to 20 Gray (Gy) in pulses of less than 500 milliseconds (ms) reaching effective dose rates of 20 to 100 Gray-per-second (Gy/S), healthy tissue experiences less damage than when irradiated with the same dose over a longer time scale, while tumors are treated with similar effectiveness. A theory that may explain this "FLASH effect" is based on the fact that radiation damage to tissue is proportionate to oxygen supply in the tissue. In healthy tissue, the ultra-high dose rate radicalizes the oxygen only once, as opposed to dose applications that radicalize the oxygen multiple times over a longer timescale. This may lead to less damage in the healthy tissue using the ultra-high dose rate.

In some examples, as noted above, ultra-high dose rates of radiation may include doses of radiation that exceed 1 Gray-per-second for a duration of less than 500 ms. In some examples, ultra-high dose rates of radiation may include doses of radiation that exceed 1 Gray-per-second for a duration that is between 10 ms and 5 s. In some examples, ultra-high dose rates of radiation may include doses of radiation that exceed 1 Gray-per-second for a duration that is less than 5 s.

In some examples, ultra-high dose rates of radiation include doses of radiation that exceed one of the following doses for a duration of less than 500 ms: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is between 10 ms and 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is less than 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second.

In some examples, ultra-high dose rates of radiation include doses of radiation that exceed one or more of the following doses for a duration of less than 500 ms, for a duration that is between 10 ms and 5 s, or for a duration that is less than 5 s: 100 Gray-per-second, 200 Gray-per-second, 300 Gray-per-second, 400 Gray-per-second, or 500 Gray-per-second.

In some examples, ultra-high dose rates of radiation include doses of radiation that are between 20 Gray-per-second and 100 Gray-per-second for a duration of less than 500 ms. In some examples, ultra-high dose rates of radiation include doses of radiation that are between 20 Gray-per-second and 100 Gray-per-second for a duration that is between 10 ms and 5 s. In some examples, ultra-high dose rates of radiation include doses of radiation that are between 20 Gray-per-second and 100 Gray-per-second for a duration that is less than 5 s. In some examples, ultra-high dose rate rates of radiation include doses of radiation that are between 40 Gray-per-second and 120 Gray-per-second for a time period such as less than 5 s. Other examples of the time period are those provided above.

In some implementations, the particle therapy systems may treat three-dimensional columns of the target using ultra-high dose rate radiation—the FLASH doses of radiation. These systems scale the ultra-high dose rate deliveries to targets using pencil beam scanning. In some examples, pencil beam scanning includes delivering a series of small beams of particle radiation that can each have a unique direction, energy, and charge. By combining doses from these individual beams, a three-dimensional target treatment volume may be treated with radiation. Furthermore, instead of organizing the treatment into layers at constant energies, the systems organize the treatment into columns defined by the direction of a stationary beam. The direction of the beam may be toward the surface of the target.

In some implementations, all or part of a column is treated before the particle beam is directed along another path through the irradiation target. In some implementations, a path through the target is all or part-way through the target. In an example, the particle beam may be directed along a path through a target and not deviate from that path. While directed along that path, the energy of the particle beam is changed. The particle beam does not move as its energy changes and, as a result, the particle beam treats all or a part of an interior portion of the target that extends along a length of the particle beam and along a width of the beam spot. The treatment is thus depth-wise along a longitudinal direction of the beam. For example, a portion of the target treated may extend from a spot of the beam at the surface of the target down through all or part of an interior of the target. The result is that the particle beam treats a three-dimensional columnar portion of the target using an ultra-high dose rate of radiation. In some examples, the particle beam may never again be directed along the same three-dimensional columnar portion more than once.

In some implementations, an irradiation target may be broken into micro-volumes. Although cubical micro-volumes may be used, the micro-volumes may have any appropriate shape, such as three-dimensional orthotopes, regular curved shapes, or amorphous shapes. In this example, each micro-volume is treated through delivery of FLASH radiation by column in the manner described herein. For example, column depths of a micro-volume may be treated with radiation by using energy degrader plates to change the beam energy or by controlling a variable-energy synchrocyclotron to change the beam energy. After an individual micro-volume has been treated, the next micro-volume is treated, and so forth until the entire irradiation target has been treated. Treatment of the micro-volumes may be in any appropriate order or sequence.

The particle therapy system described herein may deliver FLASH radiation by columns in the manner described in U.S. Patent Publication No. 2020/0298025 titled "Delivery Of Radiation By Column And Generating A Treatment Plan Therefor", the contents of which are incorporated herein by reference, particularly the contents relating to FIGS. 2, 11, 12 to 19, 33 to 43B thereof and the accompanying descriptions.

The particle therapy system described herein may fit within a LINAC vault. The LINAC vault may be shielded using lead or other appropriate materials such as concrete, borated polyethylene, and/or steel. In this regard, particles, such as protons, that are created by the particle accelerator but do not reach the irradiation target create secondary radiation through the production of high energy neutrons. In some implementations, the gantry described herein, which includes energy selection using an energy degrader that is downstream of the beamline, is configured to transmit more than 70% of the proton beam even at low energies. In this regard, in some implementations, the particle beam is at the maximum energy and fixed energy of the accelerator until just upstream of isocenter (at the inner diameter of the toroid) where it is reduced in energy by a dynamic range shifter. That is, the particle beam is at the maximum energy of the accelerator as the particle beam enters the nozzle. Due to the high beam delivery efficiency (e.g., 70 to 100%) of this system architecture, which maintains a low stray radiation from the accelerator and energy modulation, the accelerator can be located within the treatment room vault as shown in FIG. 8

In contrast, some particle therapy systems employ energy selection systems that result in significant production of high-energy neutrons and that discard more than 99% of the proton beam at lower energies. Beamline efficiency may enable a "single room" solution that puts the particle accelerator, beamline, and patient all inside a single vault. Within this vault, the particle accelerator may include shielding, but separate compartments in the vault containing the patient and the particle accelerator, respectively, need not be shielded from each other. In other words, in some implementations, there is no shielding that is external to the particle accelerator and the gantry that separates the particle accelerator from the patient.

In some implementations, to be capable of installing a proton therapy system in an existing vault, the vault is capable of providing the necessary shielding which may require that shielding be added. In the case of a toroidal gantry that does not rotate, shielding can be added local to the toroid along the beam plane. The shielding can be made of typical shielding materials such as concrete, borated polyethylene, and steel.

In some implementations, a particle accelerator other than a synchrocyclotron may be used in the particle therapy system described herein. For example, a cyclotron, a synchrotron, a linear accelerator, or the like may be substituted for the synchrocyclotron in the particle therapy systems described herein.

In some implementations, gantry 14 is stationary. That is, the cover and outer shell do not move relative to the patient, while the interior contents do move as described herein. In some implementations, the cover and outer shell are movable relative to the patient, for example, to position the segments at desired locations.

Operation of the example proton therapy systems described herein, and operation of all or some component thereof, can be controlled, at least in part, using a control system or controller 92 configured to execute one or more computer program products, e.g., one or more computer programs tangibly embodied in one or more non-transitory machine-readable media, for execution by, or to control the operation of, one or more data processing apparatus, e.g., a programmable processor, a computer, multiple computers, and/or programmable logic components.

All or part of the systems described in this specification and their various modifications may be configured or controlled at least in part by one or more computers such as the control system using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with configuring or controlling the systems described herein can be performed by one or more programmable processors executing one or more computer programs to control or to perform all or some of the operations described herein. All or part of the systems and processes can be configured or controlled by special purpose logic circuitry, such as, an FPGA (field programmable gate array) and/or an ASIC (application-specific integrated circuit) or embedded microprocessor(s) localized to the instrument hardware.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Elements of different implementations described may be combined to form other implementations not specifically set forth previously. Elements may be left out of the systems described previously without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A particle therapy system comprising:
a toroid-shaped gantry having a central axis, the toroid-shaped gantry comprising a cover, the cover comprising one or more segments that are rotatable at least partly around the central axis of the toroid-shaped gantry, the one or more segments being configured and controllable to move from a closed configuration to an open configuration to create an unobstructed opening in the toroid-shaped gantry;

a patient couch configured to move into the unobstructed opening;

an imaging system coupled to an interior of the toroid-shaped gantry and configured for rotation about a hole in the toroid-shaped gantry, the imaging system being configured to capture images of a patient on the patient couch; and a nozzle coupled to the interior of the toroid-shaped gantry and configured for rotation about the hole in the toroid-shaped gantry, the nozzle being configured to deliver radiation to a target in the patient based on one or more of the images.

2. The particle therapy system of claim 1, wherein the nozzle is connected via a beam conduit to a remote particle accelerator configured to output the radiation.

3. The particle therapy system of claim 2, wherein the remote particle accelerator is in a same room as the toroid-shaped gantry but not mounted to the toroid-shaped gantry.

4. The particle therapy system of claim 2, wherein the beam conduit comprises magnetics configured and arranged to direct a particle beam from an output of the particle accelerator to the nozzle.

5. The particle therapy system of claim 1, further comprising:

an arm to which the patient couch is mounted, the arm comprising a first segment, a second segment, and third segment, the first segment being rotatably coupled to the second segment, and the second segment being rotatably coupled to the third segment, the patient couch being connected to the third segment.

6. The particle therapy system of claim 5, wherein the arm is controlled to move the patient couch into the unobstructed opening when the one or more segments are moved to the open configuration so that the patient couch is in a vertex field position; and wherein the nozzle is controlled to direct radiation towards a top of a head of the patient on the patient couch.

7. The particle therapy system of claim 1, further comprising:

an arm to which the patient couch is mounted, the arm comprising at least two segments that are rotatably connected.

8. The particle therapy system of claim 7, wherein the arm is controllable to move the patient couch into the unobstructed opening so that the nozzle can direct radiation to the patient in a vertex field position.

9. The particle therapy system of claim 7, wherein the arm is controllable to move the patient couch into the unobstructed opening such that the patient couch is within both the hole and the unobstructed opening.

10. The particle therapy system of claim 7, wherein the arm is controllable to move the patient couch into the unobstructed opening such that the patient couch extends from an interior of the hole into the unobstructed opening.

11. The particle therapy system of claim 7, wherein the arm is controllable to move the patient couch into the unobstructed opening such that the patient couch extends at least part-way along a radius of the toroid-shaped gantry.

12. The particle therapy system of claim 7, wherein the arm is controllable to move the patient couch into the unobstructed opening so that the nozzle can direct radiation to a top of a head of the patient.

13. The particle therapy system of claim 1, wherein the imaging system is configured to capture three-dimensional (3D) images; and wherein the particle therapy system further comprises:

a control system to process the images and to control output of the radiation based on the images.

14. The particle therapy system of claim 13, wherein the control system is configured to control delivery of the radiation based on also on a treatment plan for the patient.

15. The particle therapy system of claim 1, wherein the unobstructed opening comprises a single quadrant of the toroid-shaped gantry.

16. A particle therapy system comprising:

a toroid-shaped gantry comprising a cover, the cover comprising one or more segments that are arranged around a central axis of the toroid-shaped gantry and that are movable from a closed configuration to an open configuration to create an unobstructed opening in the toroid-shaped gantry;

a nozzle to deliver radiation to a patient;

a patient couch that is controllable to move relative to the toroid-shaped gantry, the patient couch supporting the patient; and a control system to control movement of the patient couch into the unobstructed opening so that the patient is in a vertex field position and so that the nozzle can direct radiation to the patient in the vertex field position.

17. The particle therapy system of claim 16, wherein the patient couch is mounted to a movable arm, the movable arm comprises a first segment, a second segment, and a third segment, the first segment being rotatably coupled to the second segment, and the second segment being rotatably coupled to the third segment, the patient couch being connected to the third segment.

18. The particle therapy system of claim 16, wherein the nozzle is connected via a beam conduit to a remote particle accelerator configured to output the radiation.

19. The particle therapy system of claim 18, wherein the beam conduit comprises magnetics configured and arranged to direct a particle beam from an output of the particle accelerator to the nozzle.

20. The particle therapy system of claim 18, wherein the particle accelerator comprises a synchrocyclotron.

21. The particle therapy system of claim 20, wherein the synchrocyclotron comprises an active return system, the active return system comprising conductive coils that conduct current in a reverse direction to main superconducting coils in the synchrocyclotron.

22. The particle therapy system of claim 21, wherein the conductive coils comprise superconducting coils.

23. The particle therapy system of claim 18, wherein the remote particle accelerator is in a same room as the toroid-shaped gantry but not mounted to the toroid-shaped gantry.

24. The particle therapy system of claim 16, further comprising:

an imaging system mounted to the toroid-shaped gantry, the imaging system being configured to capture images of the patient;

wherein the control system is configured to control output of the radiation based the images.

25. The particle therapy system of claim 24, wherein the images comprise three-dimensional (3D) images.

26. The particle therapy system of claim 24, wherein the imaging system is configured to capture images of the patient prior to treatment.

27. The particle therapy system of claim 24, wherein the imaging system is configured to capture images of the patient during treatment.

* * * * *